(12) United States Patent
McCullough et al.

(10) Patent No.: US 9,161,743 B2
(45) Date of Patent: *Oct. 20, 2015

(54) QUICK CYCLE BIOPSY SYSTEM

(71) Applicant: C. R. Bard, Inc., Tempe, AZ (US)

(72) Inventors: Adam B. McCullough, Glendale, CA (US); Robert W. Kalis, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,678

(22) Filed: Apr. 21, 2014

(65) Prior Publication Data

US 2014/0228706 A1 Aug. 14, 2014

Related U.S. Application Data

(60) Continuation of application No. 13/097,361, filed on Apr. 29, 2011, now Pat. No. 8,702,621, which is a continuation of application No. 12/364,616, filed on Feb. 3, 2009, now Pat. No. 7,959,580, which is a division of application No. 11/047,953, filed on Jan. 31, 2005, now Pat. No. 7,517,321.

(51) Int. Cl.
*A61B 10/02* (2006.01)

(52) U.S. Cl.
CPC .......... *A61B 10/0275* (2013.01); *A61B 10/0283* (2013.01); *A61B 2010/0208* (2013.01); *A61B 2010/0225* (2013.01)

(58) Field of Classification Search
CPC .................................................. A61B 10/0275
USPC ........................... 600/562–567; 606/170, 171
See application file for complete search history.

(56) References Cited

U.S. PATENT DOCUMENTS 737,293 A 8/1903 Summerfeldt
1,585,934 A 5/1926 Muir
(Continued)

FOREIGN PATENT DOCUMENTS

DE 3924291 A1 1/1991
DE 4041614 C1 10/1992
(Continued)

OTHER PUBLICATIONS

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; Rev 1.
(Continued)

*Primary Examiner* — Brian Szmal

(57) ABSTRACT

A biopsy apparatus includes a cannula, a cutting sheath, and a pressure generating device. The cannula has a lumen, a proximal portion, a closed distal end, and an orifice located on a circumferential surface of the cannula. The orifice is configured to receive a tissue sample into the lumen of the cannula. The cutting sheath is coaxially disposed with the cannula. The cutting sheath is configured to be movable relative to the cannula to selectively cover the orifice. The pressure generating device is coupled to the proximal portion of the cannula. A bifurcated valve assembly is interposed between the cannula and the pressure generating device. The bifurcated valve assembly has a first valve configured to release pressure into the lumen of the cannula and has a second valve configured to facilitate an inflow of air into the pressure chamber of the pressure generating device.

11 Claims, 9 Drawing Sheets

(56) References Cited

U.S. PATENT DOCUMENTS

| | | |
|---|---|---|
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A * | 10/1985 | Markham ............... 600/566 |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A * | 12/1988 | Swartz ............... 604/22 |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,183,052 A | 2/1993 | Terwilliger |
| 5,197,484 A | 3/1993 | Kornberg et al. |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,282,476 A | 2/1994 | Terwilliger |
| 5,282,477 A | 2/1994 | Bauer |
| 5,290,253 A | 3/1994 | Kira |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |

(56) References Cited

U.S. PATENT DOCUMENTS

| | | |
|---|---|---|
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,854,706 B2 | 12/2010 | Hibner |
| 7,862,517 B2 | 1/2011 | Tsonton et al. |
| 7,871,384 B2 | 1/2011 | Thompson et al. |
| 7,883,476 B2 | 2/2011 | Miller et al. |
| 7,883,494 B2 | 2/2011 | Martin |
| 7,959,580 B2 * | 6/2011 | McCullough et al. ........ 600/566 |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,083,671 B2 | 12/2011 | Boulais et al. |
| 8,109,885 B2 | 2/2012 | Heske et al. |
| 8,157,744 B2 | 4/2012 | Jorgensen et al. |
| 8,162,851 B2 | 4/2012 | Heske et al. |
| 8,172,773 B2 | 5/2012 | Heske et al. |
| 8,206,409 B2 | 6/2012 | Privitera et al. |
| 8,277,393 B2 | 10/2012 | Miller et al. |

(56) References Cited

U.S. PATENT DOCUMENTS

| | | | |
|---|---|---|---|
| 8,313,444 B2 | 11/2012 | Thompson et al. | |
| 8,366,636 B2 | 2/2013 | Videbaek | |
| 8,430,827 B2 | 4/2013 | Nicoson et al. | |
| 8,702,621 B2* | 4/2014 | McCullough et al. | 600/566 |
| 8,702,622 B2* | 4/2014 | McCullough et al. | 600/566 |
| 8,956,306 B2 | 2/2015 | Hibner | |
| 2001/0007925 A1 | 7/2001 | Ritchart et al. | |
| 2001/0011156 A1 | 8/2001 | Viola et al. | |
| 2001/0012919 A1 | 8/2001 | Terwilliger | |
| 2001/0014779 A1 | 8/2001 | Burbank et al. | |
| 2001/0034530 A1 | 10/2001 | Malackowski et al. | |
| 2001/0044595 A1 | 11/2001 | Reydel et al. | |
| 2001/0047183 A1 | 11/2001 | Privitera et al. | |
| 2002/0016555 A1 | 2/2002 | Ritchart et al. | |
| 2002/0029007 A1 | 3/2002 | Bryan et al. | |
| 2002/0045840 A1 | 4/2002 | Voegele et al. | |
| 2002/0045842 A1 | 4/2002 | Van Bladel et al. | |
| 2002/0065474 A1 | 5/2002 | Viola | |
| 2002/0067151 A1 | 6/2002 | Tanishita | |
| 2002/0068878 A1 | 6/2002 | Jasonni et al. | |
| 2002/0082518 A1 | 6/2002 | Weiss et al. | |
| 2002/0082519 A1 | 6/2002 | Miller et al. | |
| 2002/0107043 A1 | 8/2002 | Adamson et al. | |
| 2002/0115942 A1 | 8/2002 | Stanford et al. | |
| 2002/0120212 A1 | 8/2002 | Ritchart et al. | |
| 2002/0143269 A1 | 10/2002 | Neuenfeldt | |
| 2002/0151822 A1 | 10/2002 | Burdorff et al. | |
| 2002/0156395 A1 | 10/2002 | Stephens et al. | |
| 2003/0023188 A1 | 1/2003 | Kritzman et al. | |
| 2003/0023239 A1 | 1/2003 | Burbank et al. | |
| 2003/0073929 A1 | 4/2003 | Baltschun et al. | |
| 2003/0093103 A1 | 5/2003 | Malackowski et al. | |
| 2003/0130593 A1 | 7/2003 | Gonzalez | |
| 2003/0130677 A1 | 7/2003 | Whitman et al. | |
| 2003/0163142 A1 | 8/2003 | Paltieli et al. | |
| 2003/0229293 A1 | 12/2003 | Hibner et al. | |
| 2003/0233101 A1 | 12/2003 | Lubock et al. | |
| 2004/0015079 A1 | 1/2004 | Berger et al. | |
| 2004/0019297 A1 | 1/2004 | Angel | |
| 2004/0030367 A1 | 2/2004 | Yamaki et al. | |
| 2004/0034280 A1 | 2/2004 | Privitera et al. | |
| 2004/0049128 A1 | 3/2004 | Miller et al. | |
| 2004/0054299 A1 | 3/2004 | Burdorff et al. | |
| 2004/0082915 A1 | 4/2004 | Kadan | |
| 2004/0092980 A1 | 5/2004 | Cesarini et al. | |
| 2004/0092992 A1 | 5/2004 | Adams et al. | |
| 2004/0162505 A1 | 8/2004 | Kaplan et al. | |
| 2004/0167428 A1 | 8/2004 | Quick et al. | |
| 2004/0186393 A1 | 9/2004 | Leigh et al. | |
| 2004/0210161 A1 | 10/2004 | Burdorff et al. | |
| 2004/0215103 A1 | 10/2004 | Mueller, Jr. et al. | |
| 2004/0220495 A1 | 11/2004 | Cahir et al. | |
| 2004/0230135 A1 | 11/2004 | Merkle | |
| 2004/0249278 A1 | 12/2004 | Krause | |
| 2004/0249307 A1 | 12/2004 | Thompson et al. | |
| 2004/0267157 A1 | 12/2004 | Miller et al. | |
| 2005/0004492 A1 | 1/2005 | Burbank et al. | |
| 2005/0004559 A1 | 1/2005 | Quick et al. | |
| 2005/0010131 A1 | 1/2005 | Burbank et al. | |
| 2005/0020909 A1 | 1/2005 | Moctezuma de la Barrera et al. | |
| 2005/0027210 A1 | 2/2005 | Miller | |
| 2005/0049489 A1 | 3/2005 | Foerster et al. | |
| 2005/0049521 A1 | 3/2005 | Miller et al. | |
| 2005/0054947 A1 | 3/2005 | Goldenberg | |
| 2005/0065453 A1 | 3/2005 | Shabaz et al. | |
| 2005/0080355 A1 | 4/2005 | Mark | |
| 2005/0085838 A1 | 4/2005 | Thompson et al. | |
| 2005/0088120 A1 | 4/2005 | Avis | |
| 2005/0101879 A1 | 5/2005 | Shidham et al. | |
| 2005/0113715 A1 | 5/2005 | Schwindt et al. | |
| 2005/0113716 A1 | 5/2005 | Mueller, Jr. et al. | |
| 2005/0124914 A1 | 6/2005 | Dicarlo et al. | |
| 2005/0124915 A1 | 6/2005 | Eggers et al. | |
| 2005/0165328 A1 | 7/2005 | Heske et al. | |
| 2005/0165329 A1 | 7/2005 | Taylor et al. | |
| 2005/0177117 A1 | 8/2005 | Crocker et al. | |
| 2005/0193451 A1 | 9/2005 | Quistgaard et al. | |
| 2005/0203439 A1* | 9/2005 | Heske et al. | 600/566 |
| 2005/0209530 A1 | 9/2005 | Pflueger | |
| 2005/0215921 A1 | 9/2005 | Hibner et al. | |
| 2005/0275378 A1 | 12/2005 | Canino et al. | |
| 2005/0277829 A1 | 12/2005 | Tsonton et al. | |
| 2005/0277871 A1 | 12/2005 | Selis | |
| 2005/0288605 A1 | 12/2005 | Pellegrino et al. | |
| 2006/0030784 A1 | 2/2006 | Miller et al. | |
| 2006/0074344 A1 | 4/2006 | Hibner | |
| 2006/0074345 A1 | 4/2006 | Hibner | |
| 2006/0074350 A1 | 4/2006 | Cash | |
| 2006/0113958 A1 | 6/2006 | Lobert et al. | |
| 2006/0116603 A1 | 6/2006 | Shibazaki et al. | |
| 2006/0122535 A1 | 6/2006 | Daum | |
| 2006/0129063 A1 | 6/2006 | Thompson et al. | |
| 2006/0149162 A1 | 7/2006 | Daw et al. | |
| 2006/0173377 A1 | 8/2006 | McCullough et al. | |
| 2006/0178666 A1 | 8/2006 | Cosman et al. | |
| 2006/0184063 A1 | 8/2006 | Miller | |
| 2006/0241515 A1 | 10/2006 | Jones et al. | |
| 2006/0258956 A1 | 11/2006 | Haberstich et al. | |
| 2007/0016101 A1 | 1/2007 | Feldman et al. | |
| 2007/0027407 A1 | 2/2007 | Miller | |
| 2007/0032741 A1 | 2/2007 | Hibner et al. | |
| 2007/0073326 A1 | 3/2007 | Miller et al. | |
| 2007/0090788 A1 | 4/2007 | Hansford et al. | |
| 2007/0106176 A1 | 5/2007 | Mark et al. | |
| 2007/0118048 A1 | 5/2007 | Stephens et al. | |
| 2007/0118049 A1 | 5/2007 | Viola | |
| 2007/0123797 A1 | 5/2007 | Krause | |
| 2007/0161925 A1 | 7/2007 | Quick et al. | |
| 2007/0167782 A1 | 7/2007 | Callahan et al. | |
| 2007/0167943 A1 | 7/2007 | Janssen et al. | |
| 2007/0179401 A1 | 8/2007 | Hibner | |
| 2007/0213590 A1 | 9/2007 | Squicciarini | |
| 2007/0213630 A1 | 9/2007 | Beckman et al. | |
| 2007/0213632 A1 | 9/2007 | Okazaki et al. | |
| 2007/0219572 A1 | 9/2007 | Deck et al. | |
| 2007/0236180 A1 | 10/2007 | Rodgers | |
| 2007/0239067 A1 | 10/2007 | Hibner et al. | |
| 2007/0255173 A1 | 11/2007 | Hibner | |
| 2007/0270710 A1 | 11/2007 | Frass et al. | |
| 2007/0276288 A1 | 11/2007 | Khaw | |
| 2007/0287933 A1 | 12/2007 | Phan et al. | |
| 2007/0292858 A1 | 12/2007 | Chen et al. | |
| 2007/0293788 A1 | 12/2007 | Entrekin et al. | |
| 2007/0293830 A1 | 12/2007 | Martin | |
| 2008/0004545 A1 | 1/2008 | Garrison | |
| 2008/0007217 A1 | 1/2008 | Riley | |
| 2008/0015429 A1 | 1/2008 | Tsonton et al. | |
| 2008/0021487 A1 | 1/2008 | Heisler | |
| 2008/0021488 A1 | 1/2008 | Berberich | |
| 2008/0030170 A1 | 2/2008 | Dacquay et al. | |
| 2008/0064925 A1 | 3/2008 | Gill et al. | |
| 2008/0064984 A1 | 3/2008 | Pflueger | |
| 2008/0071193 A1 | 3/2008 | Reuber et al. | |
| 2008/0079391 A1 | 4/2008 | Schroeck et al. | |
| 2008/0103411 A1 | 5/2008 | Van Bladel et al. | |
| 2008/0110261 A1 | 5/2008 | Randall et al. | |
| 2008/0135443 A1 | 6/2008 | Frojd et al. | |
| 2008/0146962 A1 | 6/2008 | Ritchie et al. | |
| 2008/0146965 A1 | 6/2008 | Privitera et al. | |
| 2008/0154151 A1 | 6/2008 | Ritchart et al. | |
| 2008/0161682 A1 | 7/2008 | Kendrick et al. | |
| 2008/0161718 A1 | 7/2008 | Schwindt | |
| 2008/0161719 A1 | 7/2008 | Miller et al. | |
| 2008/0161720 A1 | 7/2008 | Nicoson et al. | |
| 2008/0183099 A1 | 7/2008 | Jorgensen et al. | |
| 2008/0195066 A1 | 8/2008 | Speeg et al. | |
| 2008/0200833 A1 | 8/2008 | Hardin et al. | |
| 2008/0200836 A1 | 8/2008 | Speeg et al. | |
| 2008/0208194 A1 | 8/2008 | Bickenbach | |
| 2008/0215056 A1 | 9/2008 | Miller et al. | |
| 2008/0221443 A1 | 9/2008 | Ritchie et al. | |
| 2008/0221444 A1 | 9/2008 | Ritchie et al. | |
| 2008/0221478 A1 | 9/2008 | Ritchie et al. | |
| 2008/0221479 A1 | 9/2008 | Ritchie et al. | |

(56) References Cited

U.S. PATENT DOCUMENTS

| | | |
|---|---|---|
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0048533 A1 | 2/2009 | Miller |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1 | 7/2009 | Hibner et al. |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0063416 A1 | 3/2010 | Cicenas et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0222700 A1 | 9/2010 | Hibner |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0152715 A1 | 6/2011 | Delap et al. |
| 2011/0160611 A1 | 6/2011 | Ritchart et al. |
| 2012/0071787 A1 | 3/2012 | Reuber et al. |
| 2012/0095366 A1 | 4/2012 | Heske et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0238905 A1 | 9/2012 | Heske et al. |

FOREIGN PATENT DOCUMENTS

| | | |
|---|---|---|
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2004075728 A2 | 9/2004 |
| WO | 2005013830 A1 | 2/2005 |
| WO | 2006005342 A1 | 1/2006 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |

OTHER PUBLICATIONS

Merriam-Webster.com, Within—Definition and More from the Free Merriam-Webster Dictionary, downloaded Aug. 15, 2014, 3 pages.
Merriam-Webster.com, Series—Definition and More from the Free Merriam-Webster Dictionary, downloaded Aug. 15, 2014, 3 pages.
Merriam-Webster.com, Restrain—Definition and More from the Free Merriam-Webster Dictionary, downloaded Aug. 17, 2014, 3 pages.
Merriam-Webster.com, While—Definition and More from the Free Merriam-Webster Dictionary, downloaded Aug. 17, 2014, 4 pages.

* cited by examiner

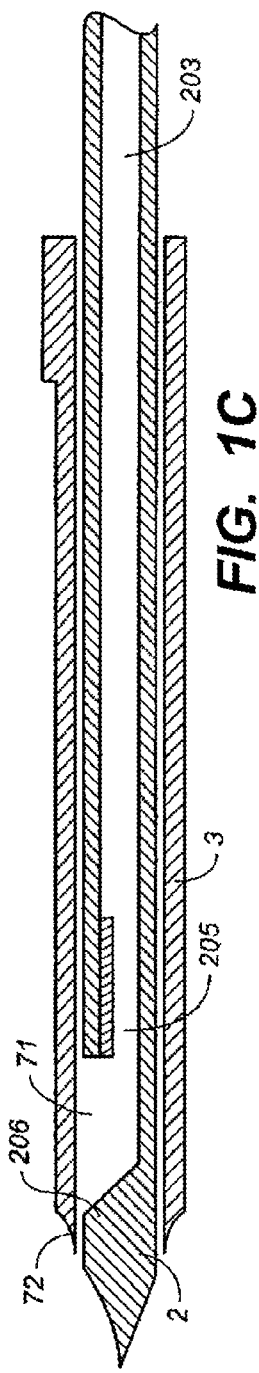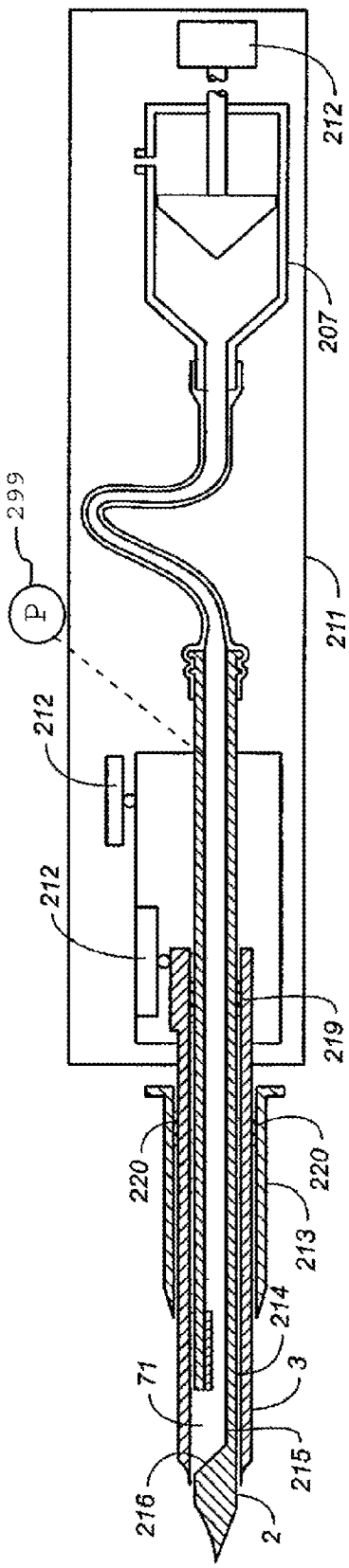

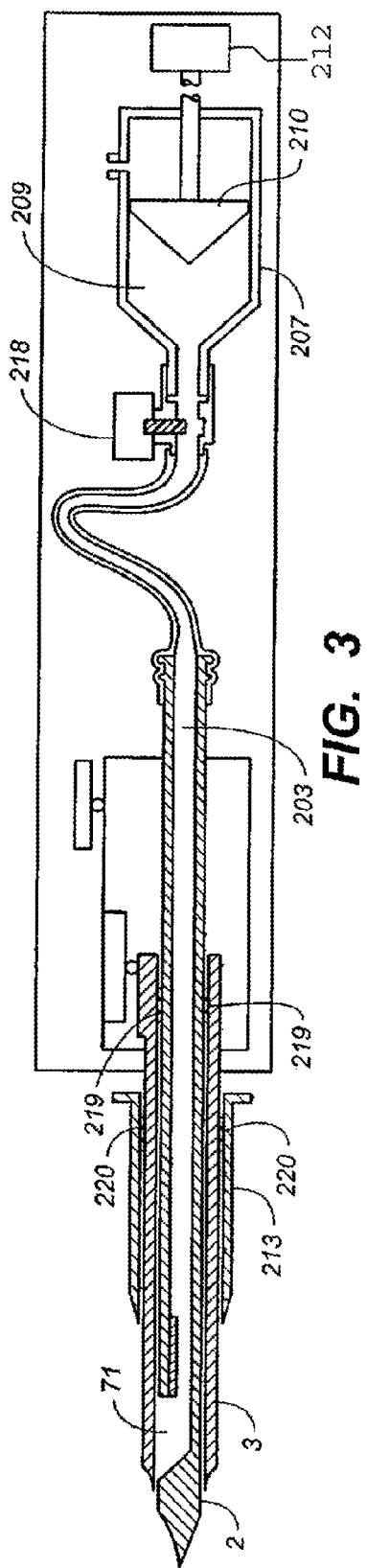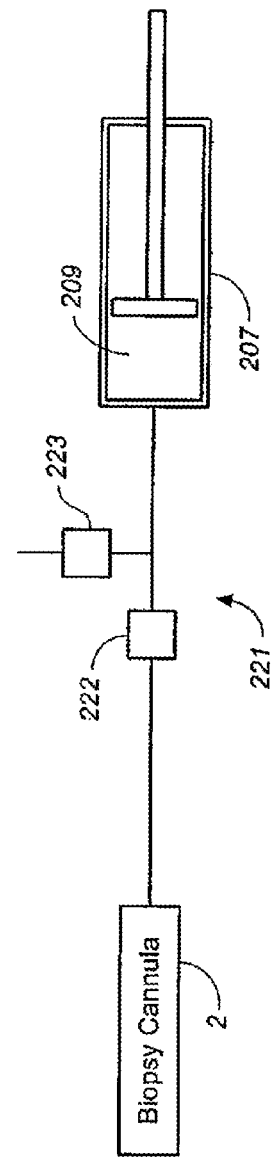
FIG. 3
FIG. 4

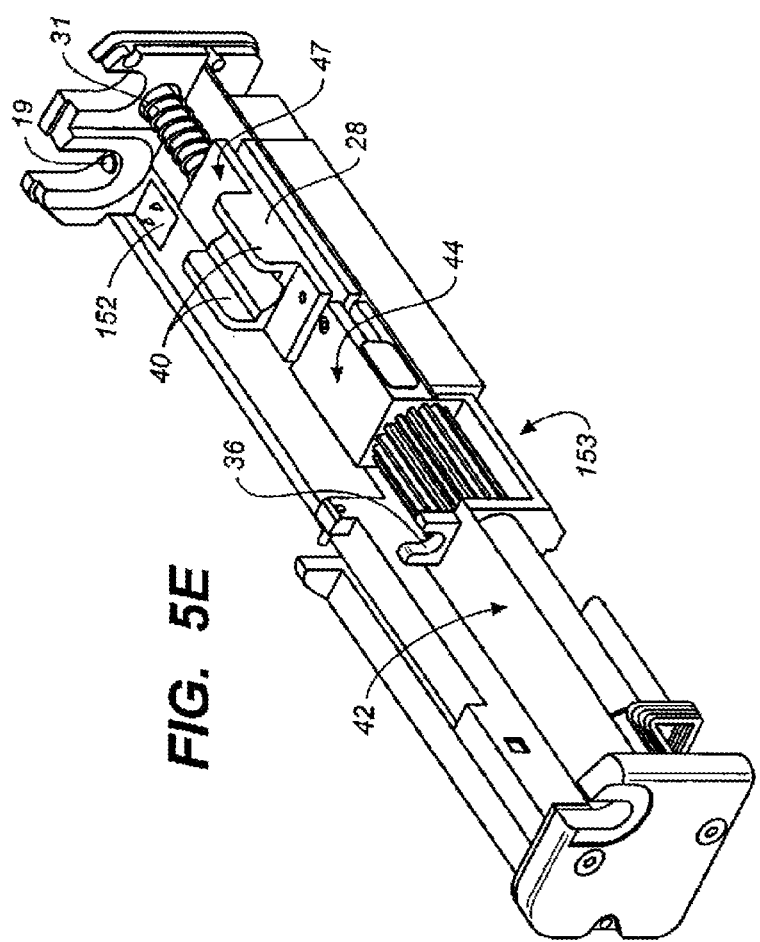
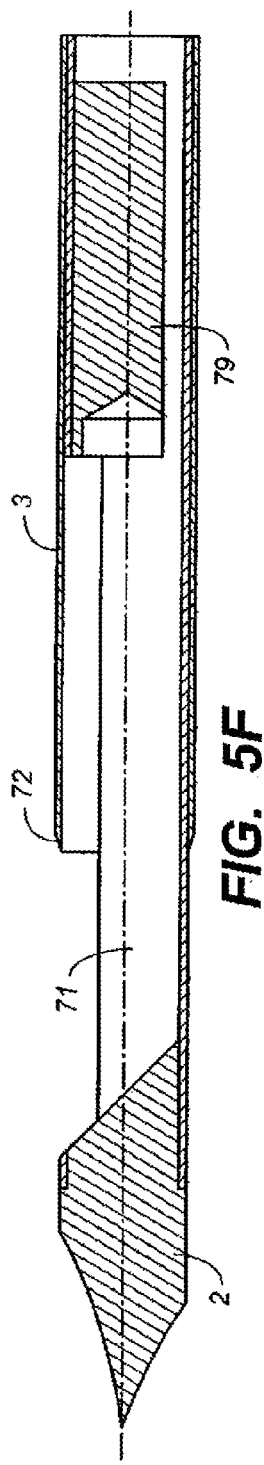
FIG. 5E
FIG. 5F

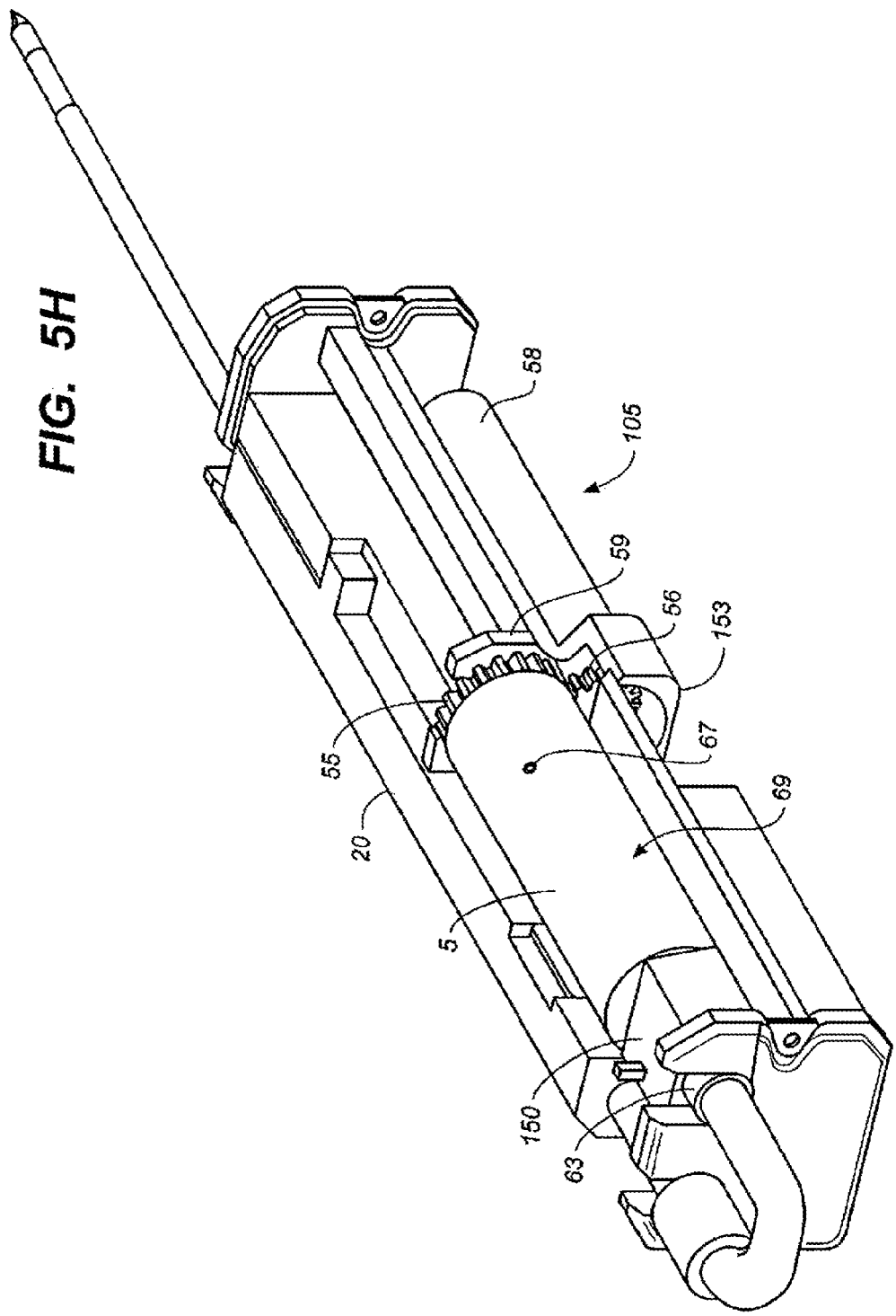

QUICK CYCLE BIOPSY SYSTEM

CROSS-REFERENCE TO RELATED APPLICATIONS

This is a continuation of application Ser. No. 13/097,361 filed Apr. 29, 2011, now U.S. Pat. No. 8,702,621, which is a continuation of application Ser. No. 12/364,616 filed Feb. 3, 2009, now U.S. Pat. No. 7,959,580, which is a divisional of application Ser. No. 11/047,953, filed Jan. 31, 2005, now U.S. Pat. No. 7,517,321, the entirety of which are hereby incorporated by reference.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

Various biopsy devices for taking tissues samples have been previously disclosed. Typically, the device comprises a hand piece, in which a portion of a hollow biopsy cannula/needle protruding from the hand piece is introduced with its sampling chamber into the tissue being investigated. A sample of the tissue is sucked into the sampling chamber by vacuum, separated by a sample separating mechanism, and then removed.

Examples of biopsy devices are disclosed in British Patent Publication No. GB 2018601A, European Patent Publication No. EP 0890 339 A1, U.S. Pat. No. 5,526,822, German Patent No. DE 40 41 614 C1, International Publication No. WO 96/28097, German Patent Publication No. DE 100 34 297 A1, International Publication No. WO 98/25522, and US Patent Publication No. 2001/0011156 A1, each of which is incorporated herein by reference in its entirety.

Integrated biopsy systems having built-in actuators for displacing a biopsy cannula and a corresponding cutting sheath and a pressure/vacuum generating device for suctioning and expelling tissue samples from the lumen of the cannula are described in U.S. patent application Ser. No. 10/500,518, entitled "BIOPSY DEVICE AND INSERTABLE BIOPSY NEEDLE MODULE" filed Jun. 29, 2004, and U.S. patent application Ser. No. 10/500,522, entitled "BIOPSY DEVICE FOR REMOVING TISSUE SPECIMENS USING A VACUUM" filed Jun. 29, 2004, each of which is incorporated herein by reference in its entirety.

Although various biopsy devices have been previously disclosed, it may be desirable to improve the reliability and efficiency of the present biopsy devices such that extraction and/or removal of the tissue sample from the tissues sample chamber within the biopsy cannula may be facilitated.

BRIEF SUMMARY OF THE INVENTION

The invention, in one form thereof, is directed to a biopsy apparatus that includes a cannula, a cutting sheath, a pressure generating device and a valve. The cannula has a lumen, a proximal portion, a closed distal end, and an orifice located on a circumferential surface of the cannula. The orifice is configured to receive a tissue sample into the lumen of the cannula. The cutting sheath is coaxially disposed with the cannula. The cutting sheath is configured to be movable relative to the cannula to selectively cover the orifice. The pressure generating device is coupled to the proximal portion of the cannula. A valve is interposed between the cannula and the pressure generating device. The valve is configured to control a flow of a fluid between the lumen of the cannula and the pressure generating device.

The invention, in another form thereof, is directed to a biopsy apparatus. The biopsy apparatus includes a cannula having a lumen, a proximal portion, a closed distal end, and an orifice located on a circumferential surface of the cannula. The orifice is configured to receive a tissue sample into the lumen of the cannula. A cutting sheath is coaxially disposed with the cannula. A pressure generating device is connected to the proximal portion of the cannula. The pressure generating device is configured to generate a pressure. A valve is interposed between the cannula and the pressure generating device. The valve is configured to control application of the pressure to the lumen of the cannula.

The invention, in another form thereof, is directed to a biopsy apparatus. The biopsy apparatus includes a housing, a removable element, and an actuator. The removable element is configured for insertion into the housing. The removable element includes a cannula having a lumen, a proximal portion, a closed distal end, and an orifice located on a circumferential surface of the cannula; a sheath coaxially disposed with the cannula; a pressure generating device coupled to the proximal portion of the cannula; and a valve interposed in fluid communication with the cannula and the pressure generating device. The actuator is located in the housing. The actuator is configured to operate the valve to build-up either positive pressure or negative pressure in the pressure generating device to a pressure level desired by an operator. The actuator is configured to operate the valve to apply built-up positive pressure or negative pressure to the lumen of the cannula.

One aspect of the invention comprises a method for facilitating the ejection/removal of a tissue sample from the tissue chamber within the biopsy cannula. The cannula may be inserted into a body of tissue within a patient to extract a sample of the tissue of interest. Once the sample tissue is pulled within the tissue chamber in the cannula through suction, the chamber is closed, severing the sample tissue from the patient's body. The cannula may then be removed from the patient's body. The tissue chamber is maintained in a closed position while the lumen of the cannula is pressurized. Once the pressure within the lumen of the cannula has reached a desired level, the tissue chamber is opened. The pressure behind the sample tissue will force the sample tissue to eject or move out of the tissue chamber. The operator may open only a distal portion of the chamber (e.g., exposing only the distal one-third or one-half of the chamber opening) to prevent the fluids from leaking through the side of the sample tissue, and force the sample tissue to exit from the partial opening. Alternatively, if the pressure is high enough, the operator may open the chamber completely.

Another aspect of the invention comprises a biopsy apparatus with an integrated valve for facilitating high and/or low pressure build-up within a pressure chamber for providing suction and/or ejection pressure to the lumen of the biopsy cannula. In one variation, the biopsy apparatus comprises a built-in pressure generator that is coupled to the proximal end of a biopsy cannula. The pressure generator may be capable of generating both a positive and a negative (e.g., vacuum) pressure within the lumen of the cannula. A valve is placed between the biopsy cannula and the pressure generator to control the fluid flow from the chamber of the pressure generator to the lumen of the biopsy cannula. An electronic system control board coupled to an actuator may be utilized to displace the biopsy cannula and its corresponding cutting sheath. The electronic system control board may also be adapted to control the pressure generator and the valve. In one application, the valve is placed in the open position when the pressure generator applies suction to the lumen of the cannula to extract a sample of the interested tissue into the chamber of the cannula. After the chamber is closed and the cannula is removed from the patient's body, the valve is closed and a positive pressure is built-up within the chamber of the pressure generating device. Once the tissue chamber has been opened, the valve may subsequently be opened to release the built-up pressure into the lumen of the cannula. The fluid inside the pressure chamber enters the lumen of the cannula and ejects the tissue sample out of the cannula. One of ordinary skill in the art having the benefit of the disclosure herein would appreciate that the valve may be utilized to build-up either positive or negative pressure inside the chamber to various pressure levels as desired by the operator. The valve may then be released to cause a sudden increase or decrease in pressure within the lumen of the cannula.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 1C illustrates the distal portion of the biopsy apparatus of FIG. 1A with the cutting sheath advanced over the tissue chamber.

FIG. 2 illustrates a biopsy apparatus integrated within a housing with actuators for moving the biopsy cannula and its corresponding cutting sheath.

FIG. 3 illustrates another variation of a biopsy apparatus with an integrated valve for controlling fluid flow from the pressure generator to the lumen of the biopsy cannula.

FIG. 4 is a diagram illustrating yet another variation of the biopsy apparatus where a bifurcating valve system is utilized to control pressure distribution within the apparatus.

FIG. 5E shows the main housing/frame of the biopsy apparatus of FIG. 5A with its corresponding actuator/driver and spring-load displacement system. The components are shown without the housing cover, and with the spring-load displacement system in an uncocked condition.

FIG. 5F is a cross-sectional view of the biopsy cannula and its corresponding cutting sleeve of the biopsy apparatus of FIG. 5A. The cannula is shown with its tissue sample chamber partially opened.

FIG. 5H shows the pressure generating device integrated with the biopsy cannula carrier and installed on the main housing (perspective view).

DETAILED DESCRIPTION OF THE INVENTION

The following detailed description should be read with reference to the drawings, in which identical reference numbers refer to like elements throughout the different figures. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated, this invention need not be limited to applications in humans. As one of ordinary skill in the art would appreciate, variations of the invention may be applied to various other animals and plants as well. Moreover, it should be understood that embodiments of the present invention may be applied in combination with various imaging devices (e.g., ultrasound, X-ray, etc.) for guiding the surgeon on the placement of the biopsy needle/cannula within a patient's body.

Taking biopsy of a tumor tissue is used herein as an example application of the biopsy apparatus and method disclosed herein. In light of the disclosure herein, one of ordinary skill in the art would appreciate that variations of the apparatus and/or method may be applicable for extracting samples from various types of tissues within the human body.

It must also be noted that, as used in this specification and the appended claims, the singular forms "a," "an" and "the" include plural referents unless the context clearly dictates otherwise. Thus, for example, the term "an actuator" is intended to mean a single actuator or a combination of actuators, "a fluid" is intended to mean one or more fluids, or a mixture thereof. Furthermore, the words "proximal" and "distal" refer to directions closer to and away from, respectively, a physician operating the biopsy cannula, with the tip end (i.e., distal end) placed inside the patient's body. Thus, for example, the cannula end placed in the tissue of the patient would be the distal end of the cannula, while the cannula end outside the patient's body would be the proximal end of the cannula.

Figure 1A:
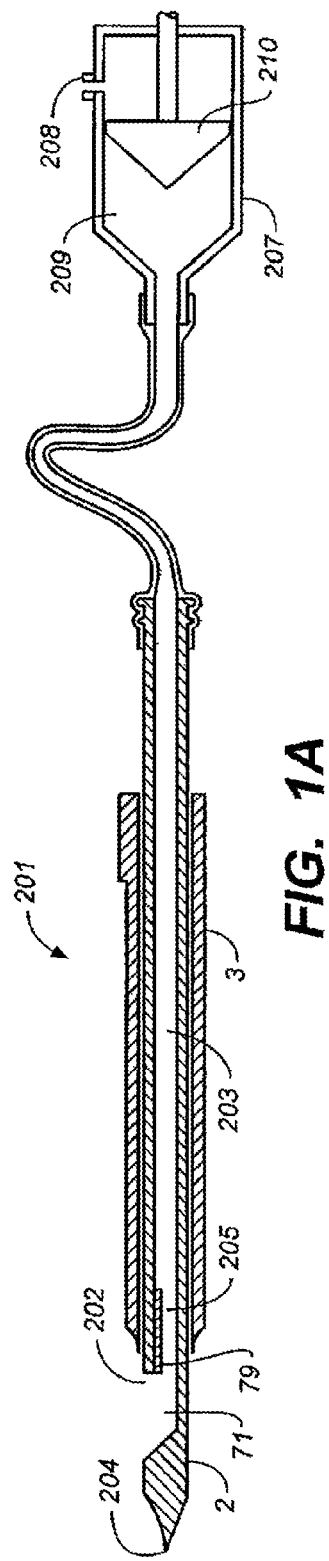
FIG. 1A is a cross-sectional view of a variation of a biopsy apparatus where the biopsy cannula is connected to a pressure generating device.
Figure 1B:
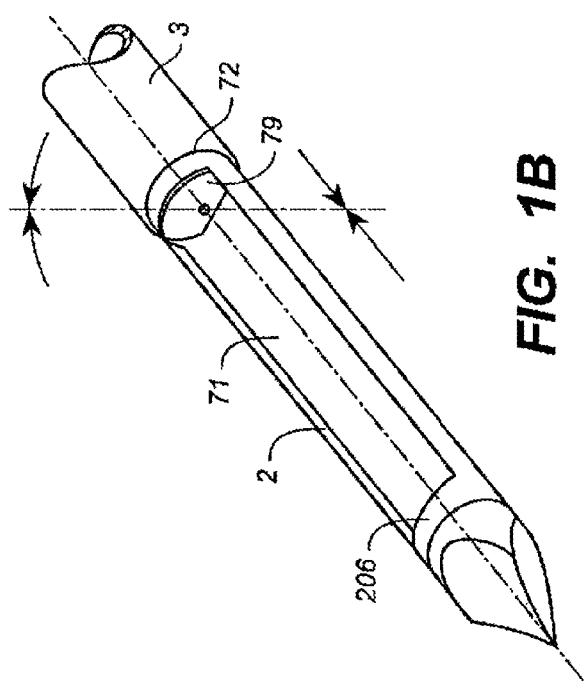
FIG. 1B is a perspective view of the distal portion of the biopsy cannula of FIG. 1A. The cutting sheath is shown in a retracted position exposing the tissue chamber in the lumen of the biopsy cannula.

One aspect of the invention comprises a method of building up a pressure inside the biopsy apparatus to eject a tissue sample captured in the chamber of the device. In one variation, the method comprises providing a biopsy cannula having a closed distal end and an orifice located on a circumferential surface of said cannula. An example of such a biopsy apparatus 201 is shown in FIG. 1A. The orifice 202 on the circumferential surface of the cannula forms the opening for access of a tissue chamber 71 at the distal end of the lumen 203 of the cannula 2, as shown in FIG. 1A. A cutting sheath 3 is slidably disposed on the cannula 2. The cannula 2 with orifice 202 covered by the sheath 3, as shown in FIG. 1C, can be inserted into a body of tissue inside a patient. A needle or cannula guide may be first inserted into the tissue to guide the insertion of the biopsy cannula. A mechanical displacement mechanism, such as spring loaded lever or driver, may be used to eject and/or force the biopsy cannula 2 and its corresponding cutting sheath 3 into the desired body of tissue. A negative pressure (pressure lower than either tissue surrounding the cannula and/or the atmospheric pressure) is generated inside the lumen of the cannula. The negative pressure may be generated prior, during and/or after the insertion of the cannula/sheath unit into the tissue of interest.

Once the distal end 204 of the cannula 2 is in place, the cutting sheath 3 may be retracted toward the proximal end of the cannula to expose the orifice 202. A suction draws a portion of the desired tissue into the tissue chamber 71 within the lumen of the cannula 2. In one particular design, a stopper 79 is positioned within the lumen 203 of the cannula 2, proximal to the orifice on the cannula. The distal end of the stopper along with the wall of the cannula lumen forms a tissue chamber 71 at the distal portion of the cannula. The stopper 79 partially blocks the lumen to allow fluid flow in the unobstructed portion 205 of the lumen, but to prevent the captured tissue sample from migrating in the proximal direction. Once the tissue is captured within the tissue chamber 71, the cutting sheath 3 may be advanced in a distal direction to cover the orifice 202 on the cannula 2, which acts to sever the sample tissue from the body of tumor tissue in the patient. The distal tip 72 of the cutting sheath 3 may be advanced past the distal edge 206 of the tissue chamber to achieve a clean separation between the sample tissue and the primary body of tissue of interest. The cannula 2 and its corresponding cutting sheath 3 may then be removed from the patient's body.

While the cutting sheath is closed, a positive pressure (a pressure higher than atmospheric pressure) is generated within the lumen 203 of the cannula 2. As shown in FIG. 1A, a pressure generator 207, such as a cylinder with a single piston, may be utilized to generate the negative and positive pressure within the lumen 203 of the cannula 2. In the particular example shown in FIG. 1A, to release the negative pressure inside the lumen of the cannula, the piston 210 may be retracted past the release port 208 such that the pressure within the lumen 203 of the cannula 2 and the pressure chamber 209 of the pressure generator can normalize. The piston 210 may then be advanced in the distal direction to compress air in the lumen 203 of the cannula 2. Once the positive pressure within the lumen 203 reaches a predefined level (e.g., the piston has been advanced a predefined distance; a pressure sensor 299 is utilized to verify the pressure inside the lumen, etc.), the cutting sheath 3 is retracted in a proximal direction to expose the tissue sample within the tissue chamber 71. One may open the chamber 71 in increments. For example, one may initially open the chamber 71 only the distal one-third or one-half thereof. Alternatively, one may fully open the chamber at once. The pressure that has built-up behind the tissue sample will force the tissues sample to eject out of the tissue chamber 71.

Referring to FIG. 2, a variation of the biopsy apparatus is shown with a housing 211 and integrated actuators/drivers 212 for displacing the cannula 2, the corresponding cutting sheath 3, and the piston 210. A spring-loading mechanism or other similar ejector may be implemented for the insertion of the biopsy cannula 2 and its corresponding cutting sheath 3. An electronic controller board with an on-board processor may be utilized to control and synchronize the action of all the associated actuator and displacement mechanisms in the integrated biopsy apparatus. An optional needle/cannula guide 213 may be utilized to guide the insertion of the cannula/sheath unit. One of ordinary skill in the art would appreciate that other pressure/vacuum generating devices may also be implemented in place of the cylinder/piston unit.

By changing the program control parameters in an integrated biopsy device, such as the one shown in FIG. 2, air pressure can be accumulated and released all at once instead of in a gradual manner. For example, before the chamber is opened, the controller may depress the piston within the cylinder by a predetermined distance to generate a positive pressure and hold the piston in place to maintain the pressure. Thereafter, the tissue chamber is exposed by sliding open the chamber cover (i.e., cutting sheath). As soon as the tissue sample fits through the opening space, it will shoot out of the biopsy cannula. In the particular design shown in FIG. 2, because the lumen opening 214 for delivering the pressure is at the proximal end of the tissue chamber 71 close to the base 215 of the chamber, opening of the chamber cover at the distal end 216 first may prevent premature leakage of the fluid pressure and allow the fluid pressure to push the captured sample all the way through the chamber, and in the process clear the chamber of any particles.

In another aspect of the invention, as shown in FIG. 3, a valve 218 is implemented to allow positive or negative pressure to build-up with the pressure generation device 207 such that instant pressure increase or decrease can be realized with the release/opening of the valve 218. Alternatively, a large positive or negative pressure may be created within the pressure chamber 209 of the pressure generating device 207, and the valve 218 may be utilized to control the release of the positive/negative pressure into the lumen of the cannula 2. In addition, a seal (e.g., O-ring) 219 may be placed between the cannula and its corresponding cutting sheath to prevent the leakage of negative pressure that has been generated in the surrounding tissue when the tissue chamber 71 is opened inside the patient's body. An additional seal (e.g., O-ring) 220 may also be provided between the cannula guide 213 and the cutting sheath 3.

In one example application, with the assistance of an ultrasound imaging device, a cannula guide 213 is inserted into a body of tumor tissue within the patient's body. The cannula 2 with its tissue chamber 71 covered and placed in a spring-loaded cocked position is inserted into the cannula guide and advanced toward the tissue. The spring-loaded cannula is then released, shooting into the tumor tissue. With the cannula 2 in place, the piston 210 in the pressure generating device 207 is retracted to regenerate a negative pressure within the lumen of the cannula 2. The cutting sheath is subsequently retracted to expose the orifice to the tissue chamber. A sample of the tissue is suctioned into the tissue chamber 71. A delay may be built into the control protocol to ensure that the tissue chamber 71 is loaded before the cutting sheath 3 is slid back into the closed position. In an alternative approach, the valve may be closed and a negative pressure generated within the chamber 209 of the pressure generating device 207 prior to or after the cutting sheath is retracted and the chamber is opened. With the cannula 2 inserted inside the tumor tissue and the orifice to the tissue chamber in an open position, the valve 218 may be opened to provide the suction to capture a sample of the tumor tissue within the tissue chamber.

Once the sample of tissue is suctioned into the tissue chamber 71, the cutting sheath 3 is advanced forward of the orifice of the tissue chamber 71, severing the sample tissue in the chamber from the body of tumor tissue. With the sample tissue secured in the tissue sample chamber 71, both the cannula 2 and the cutting sheath 3 are withdrawn from the patient's body. Either prior to, during, or after the cutting sheath 3 is retracted to expose the captured tissue sample, the valve 218 may be closed and positive pressure generated in the pressure chamber 209 inside the pressure generating device 209 by compressing the piston 210. With the cutting sheath 3 retracted and the orifice of the tissue sample chamber 71 at least partially exposed, the valve 218 may then be released to direct a positive pressure into the lumen 203 of the cannula 2 to force the sample tissue out the cannula 2. The steps described above may be executed through manual control, or may be programmed into an electronic controller that is linked with the actuators/drives to synchronize the various components and carryout the desired procedure.

FIG. 4 illustrates another valve implementation to control pressure build-up and release within a pressure chamber. In this configuration, a bifurcate 221 with two valves 222, 223 are provided between the pressure generating device 209 and the biopsy cannula 2. A first valve 222, which is inline with the cannula 2 and the pressure generating device 207, controls the release of pressure into the lumen of the cannula 2. A second valve 223 on the bifurcating branch is provided for releasing pressure from the system or allowing inflow of air into the pressure chamber 209. The valves 222, 223 may be coupled to actuators that are linked to an electronic system controller.

Figure 5A:
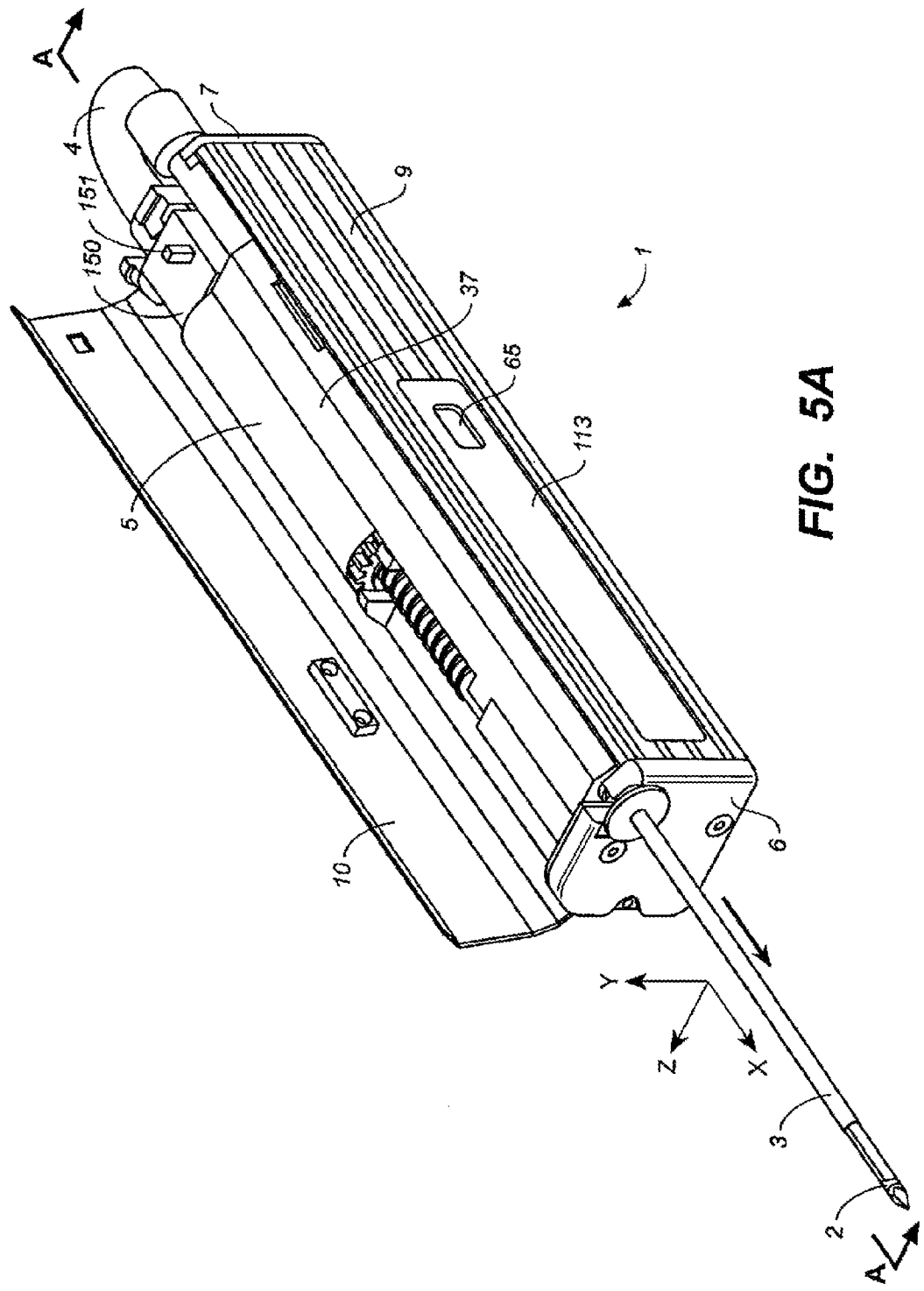
FIG. 5A shows another variation of a biopsy apparatus with its housing cover opened (perspective view).

A particular variation of a biopsy apparatus is illustrated in FIG. 5A. Integrated in a housing interior of a hand piece 1 are all devices and components required to perform a vacuum biopsy (FIG. 5A), so that no cables or lines are required going from the housing of the hand piece to other external supply devices. Thus, the hand piece 1 constitutes a complete vacuum biopsy apparatus, which is freely moveable in all directions. The apparatus is shown with an optional valve 150 for controlling the fluid flow from the vacuum/pressure generating unit 5, through the connection element 4, to the proximal end of the biopsy cannula. The valve may further comprise a control knob 151 to allow the operator to manually open the valve and release the pressure inside the pressure chamber of the vacuum/pressure generating unit 5. Alternatively, the valve 150 may be coupled to an actuator, which is linked to an electronic system control board. The electronic system control board may open and close the valve through controlling the actuator. The actuator may be positioned below the base board with levers or other mechanical interface 152 (FIG. 5B), extending above the base board, for coupling with the valve mechanisms. One of ordinary skill in the art, having the benefit of this disclosure, would appreciate that other fluid flow control mechanisms may be implemented in place of the valve to control positive and/or negative pressure build-up inside the pressure chamber of the vacuum/pressure generating unit 5.

In applications where pressure build-up is regulated by keeping the tissue chamber closed during pressurizing and depressurizing of the pressure generating device, the apparatus 1 may be fabricated without the control valve 150, and the connection element 4 may be directly connected to the pressure generating device 5.

Figure 5B:
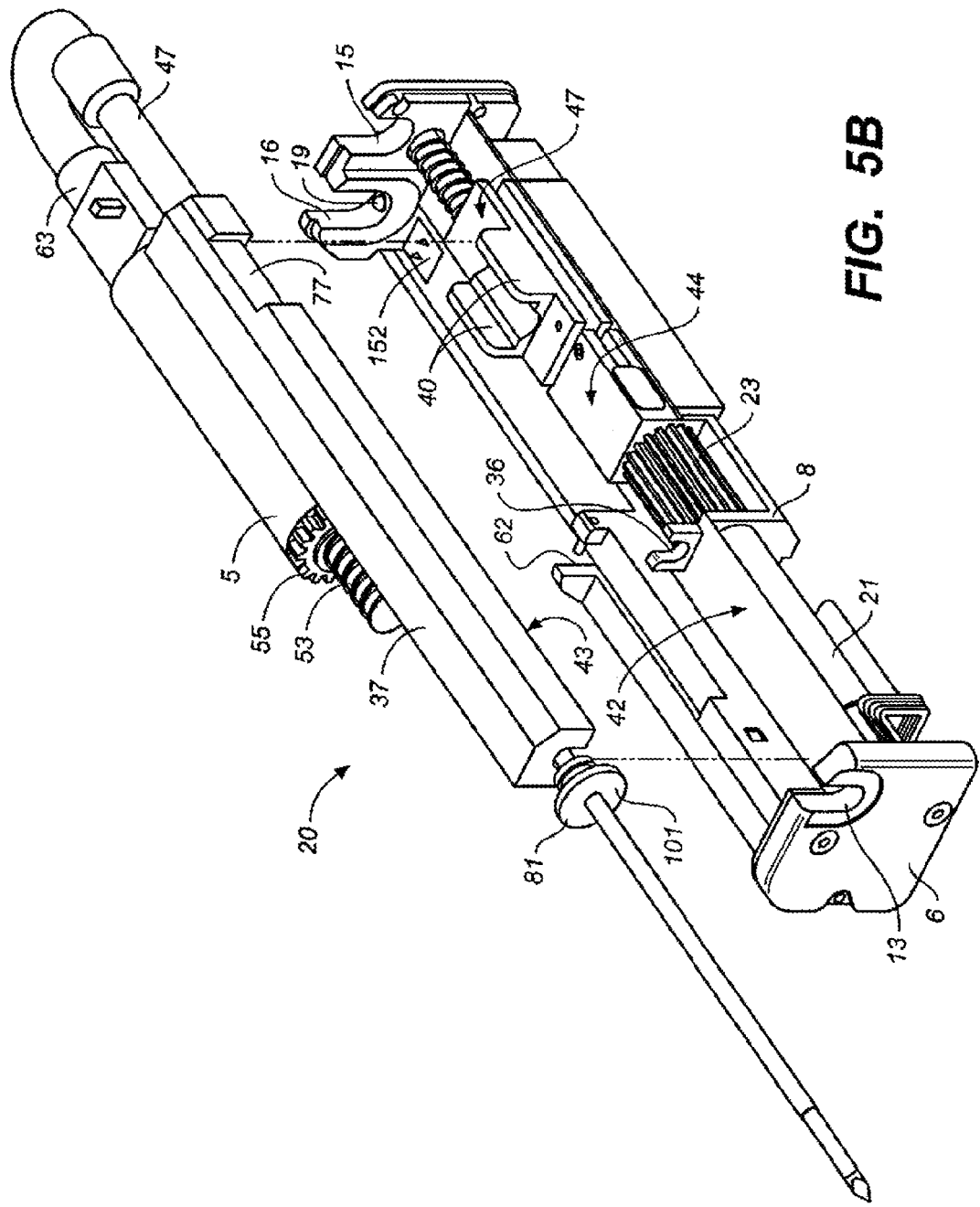
FIG. 5B shows a partially disassembled biopsy apparatus of FIG. 5A. The primary components are fixed to a housing (shown without the housing cover) and the replaceable biopsy unit is shown separated from the main housing (perspective view).

From the distal part of the distal end cover 6 protrudes the distal part of the hollow biopsy cannula 2, with the cutting sheath 3 surrounding it coaxially, which is required to remove the tissue sample. Usually, a coaxial cannula guide is placed into the tissue first, into which the biopsy cannula 2 with cutting sheath 3 is inserted. Outside the proximal end cover 7 of the housing there is arranged a connection element 4 (e.g., a transparent flexible hose) which connects the valve and the vacuum pressure generating device 5, arranged in parallel with the biopsy cannula, to the interior cavity of the biopsy cannula 2. The hollow connection element 4 is situated in immediate proximity to the end cover 7 of the housing. The biopsy cannula with cutting sheath and additional elements, arranged in a biopsy cannula carrier 37, forms together with the connection element 4 and the vacuum pressure generating device 5 an element 20, easily inserted or taken out at the top, which is replaced as necessary (FIG. 5B). The housing cover 10 is opened for this purpose. As FIG. 5B in particular shows, the biopsy device can be divided into parts which are firmly connected to the housing (disinfected parts) and a removable element 20 (sterile part). While the parts firmly connected to the housing are merely disinfected, the removable element 20 may come in a sterile package and can be replaced as necessary, especially for each new patient.

Figure 5C:
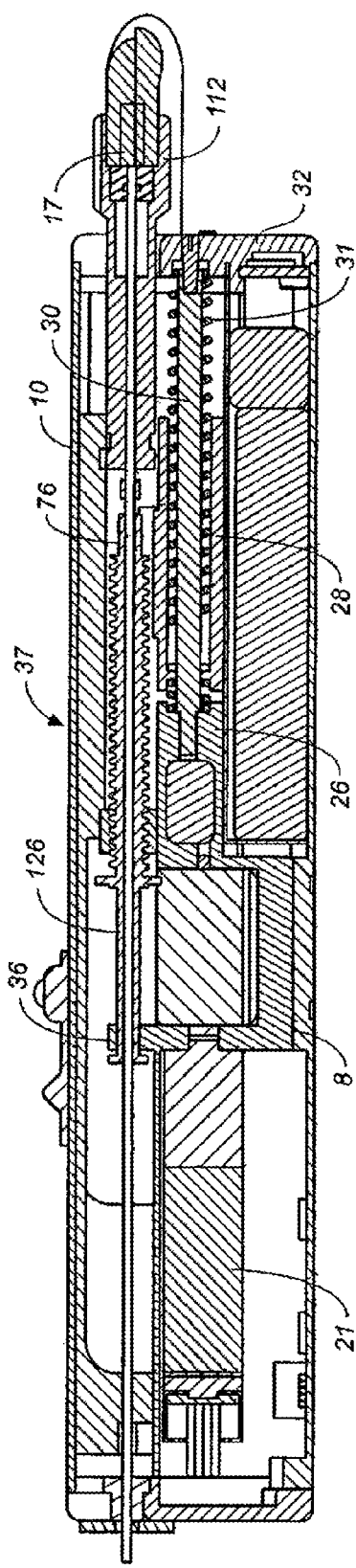
FIG. 5C shows a lengthwise section of the biopsy apparatus of FIG. 5A.

The removable insert element 20, comprising a vacuum pressure generating device 5, elastic connection element, biopsy cannula carrier 37 with cannula and cutting sheath and additional elements connected to it, also contains a guide roller 81 mounted on the cannula. This unit, including an insert aid, comes in a sterile package. The plunger in the syringe body of the vacuum/pressure generating unit 5 comes slightly (about 1-2 mm) displaced from the syringe bottom and the sample removal chamber 71 of the biopsy cannula 2 may be open to improve sterilization within the chamber. After opening the housing cover 10, the carrier element 37, including biopsy cannula 2, cutting mechanism 3, and other parts connected with it, such as the vacuum pressure generating device 5 hooked up to the connection element 4, is inserted into the connection element provided for this (FIG. 5B). FIG. 5G shows the biopsy cannula carrier from the under side with the components, for coupling the biopsy cannula 2 and the cutting sheath 3 to the gear motor 21, exposed.

During the insertion process, the operator should check to ensure that the gear 74 engages with the teeth of the toothed roller 23; that the cutting sheath is inserted from above into the U-shaped holder 36, and at the same time that the brackets 40 of the tension slide are introduced into the recesses 77 of the carrier element; the guide roller 81 is inserted in the passage 13, so that the flanks 101 and 102 embrace the distal end cover 6. The cutting sheath 3 is mounted in the guide roller 81, able to move lengthwise and turn freely; the guide roller 81 itself, however, can no longer move relative to the cutting sheath 3 after being inserted in the distal end cover 6, as illustrated in FIG. 5B. The vacuum pressure generating device 5 is then inserted onto the base block 8, with its connection piece 63 inserted into the U-shaped, upward-open passage 16 on the base block 8. The connection piece 63 lies above the switch pin 19.

When the housing cover is closed, the connection piece 63 is forced downward and activates the miniature switch by the switch pin 19 built into the end cover of the housing. This activates the electrical control system, which is indicated by blinking of the reset diode on the control panel located at the left side 113 of the hand piece 1. The reset diode at first blinks yellow, which means that the positioning of the individual elements, i.e., the inserting process, is not yet finished; the DC gear motor 21 first open the sample chamber 71 all the way (at which point the motor feels resistance and calibrate that point), it then rotates the other direction a certain predetermined number of revolutions until the sample chamber 71 is closed with the cutting sheath 3. This occurs by twisting the threaded casing connected to the cutting sheath. The cutting sheath moves in the distal direction until the gear 74 comes to bear against the inside of the holder 36. In one variation, the controller is able to calibrate the displacement by counting the number of the rotation during the reset sequence, and then uses that information to start and stop the rotation rather than relying on the physical stops. After closing the sample removal chamber, the plastic disk 78 bears against the holder 36 (inside). During this process, or before or after it, the DC gear motor 58 brings the syringe plunger to bear against the syringe bottom. FIG. 5H shows the removable insert element 20 inserted on the main housing frame 153.

After the starting positions have been established for the vacuum pressure generating device and the biopsy cannula/cutting sheath, the cocking diode lights up yellow and the sample removal diode light up green and the reset diode goes out. The operator must now decide whether to initiate the cocking of the tension slide or to remove an additional sample, e.g., because he has already previously removed one tissue sample. If the operator presses the cocking button, the cocking of the tension slide is initiated; the cocking diode blinks yellow, the pierce diode blinks green, and the sample removal diode goes out. By pressing the cocking button, the electrical DC gear motor 21 receives current and the DC gear motor actuates the toothed roller 23. The gear 74 meshing with the toothed roller 23 turns the spindle shaft and at the same time the cutting sheath 3 connected to it. Since the spindle nut 75 is press-fitted in the biopsy cannula carrier 37 and the gear 74 is supported against the holder 36, which is firmly connected to the housing by the base block 8, the turning of the threaded spindle casing 73 has the effect of moving the biopsy cannula carrier in the proximal direction.

At the same time, the biopsy cannula 2 connected to the biopsy cannula carrier by the bearing element 49 is carried along, resulting in the tip of the biopsy cannula moving into the cutting sheath. The biopsy cannula carrier 37 is displaced in the proximal direction by the recess/bracket connection of the tension slide against the action of the spiral spring 31 until the lever of the locking element is forced into the recess of the tension slide by the spring. The tension slide is locked in this position. The gear motor receives the control command that the locking position has been reached, e.g., via a photocell installed in the sliding surface of the cover plate or based on the number of rotations by the motor, which interacts with the retracted biopsy cannula carrier; the direction of turning of the motor is reversed and the cutting sheath is displaced in the proximal direction by the amount that the cutting sheath had moved beyond the tip of the biopsy cannula by the movement of the tension slide and the biopsy cannula.

At the end of this step, the cutting sheath completely closes the sample removal chamber, as at the start of the cocking process. The locking diode lights up green; the blinking of the cocking diode goes out. Now, the biopsy cannula of the biopsy mechanism is inserted, for example, in a previously mounted coaxial cannula. The proximal end of the mounted coaxial cannula receives a seal, designed so that it seals off the space between cutting sheath and cannula, on one hand, and allows an easy insertion of the biopsy cannula with cutting sheath, on the other. The seal ring prevents air from the outside getting sucked in through the space between cannula and cutting sheath. The seal ring likewise prevents fluid (cytological material) from escaping after the biopsy cannula is introduced or inserted. Thus, the possibility of the disinfected hand piece 1 getting dirty is nearly precluded; on the other hand, the flank 101 of the sterile guide roller 81 prevents the sterile cannula from getting dirty by reason of the hand piece 1. The tip of the biopsy cannula is brought up in the cannula to the tumor and, after being correctly positioned, thrust into the tumor.

The shot is triggered by pressing the activation button on the control interface panel. This has the result of swiveling the double-arm lever about the axis to release the tension slide. The tension slide is hurled in the distal direction by spring action. The sample removal diode lights up green and the cocking diode goes out. By operating the program button, the sample removal sequence is enabled; the sample removal diode blinks green. At first, the DC gear motor 58 will activate the vacuum pressure generating device. The plunger of the vacuum pressure generating device is moved in the direction of the base block, i.e., away from the bottom of the syringe, until it reaches a position just before clearing the ventilation borehole 67. The vacuum is generated in the system. After reaching its end position, the system activates the motor 21, the cutting sheath which closes the sample removal chamber is opened via the gear/spindle drive. During the opening process, the partial vacuum prevailing in the system sucks in the tissue and any cytological fluid (cytological material) into the sample removal chamber. Cytological fluid may also flow due to the vacuum in the biopsy cannula cavity and the vacuum pressure generating device.

It has proven to be advantageous to direct the partial vacuum by the stopper 79 primarily at the lower region, the lower side, of the sample removal chamber, and the stopper 79 will prevent or impede tissue from getting into the biopsy hollow cannula. When the sample removal chamber is fully open—the tissue sample is accommodated in the sample removal chamber—the gear motor 21 is reversed and the sample removal chamber 71 is closed. By turning the cutting sheath, the tissue is separated by the cutting edge 72 of the sheath 3 during the closing process. In order to reliably cut through the tissue filaments, it is advantageous to move the cutting sheath 3 beyond the distal end of the sample removal chamber (around 2 mm). In order to accomplish this, it is only necessary to program accordingly the microprocessor where the control data is kept. Because of the special configuration of the sample removal chamber and thanks to the vacuum applied, the tissue sample is held in the chamber without torsion, so that the tissue sample is not twisted or turned by the rotating and lengthwise moveable cutting sheath 3 which surrounds the biopsy cannula on the outside, as described.

After the sample removal chamber is closed, the DC gear motor is activated for the vacuum generating unit 5. The plunger is first retracted far enough to clear the ventilation opening 67 (FIG. 5F). After the vacuum is dissipated in the system, the plunger travels toward the vacuum bottom until the ventilation borehole 67 is again closed, in order to prevent the outflow of bodily fluid (cytological fluid). The blinking of the sample removal diode goes out. The ejection diode lights up yellow. The biopsy cannula with closed sample chamber is extracted from the cannula guide.

After the removal of the biopsy unit and providing a vessel to receive the tissue sample and fluid, the program button is again operated and the ejection diode starts to blink. First, the DC gear motor 58 of the vacuum pressure generating device is activated while the sample removal chamber remains closed. The turning direction of the DC gear motor 58 remains and the threaded spindle with plunger moves in the direction of the syringe bottom, so that now an excess pressure is created in the system. After this, the gear motor 21 of the cutting sheath is operated to open the sample removal chamber roughly halfway. As soon as the sample fits through the opening it will shoot out of the biopsy chamber.

In a system with a built-in valve 150, an alternative approach may be used to eject the sample from the sample removal chamber. After the removal of the biopsy unit from the patient, the actuator coupled to the valve is activated to close the valve 150. With the valve 150 closed, the DC gear motor 58 of the vacuum pressure generating device is activated. The turning direction of the DC gear motor 58 remains and the threaded spindle 53 with plunger moves in the direction of the syringe bottom, so that now an excess pressure is created in chamber of the pressure generating device. After this, the gear motor 21 of the cutting sheath is operated to open the sample removal chamber roughly halfway. The actuator couple to the valve is activated to open the valve and release the pressure into the biopsy cannula, and force the sample out the biopsy chamber 71.

With the release of the excess pressure build-up in the vacuum/pressure generating unit 5, the sample is forced out due to the a pressure pulse and ejects into a waiting laboratory vessel even when the sample removal chamber is halfway open, and at the same time the chamber of the vacuum pressure generating device, the biopsy cannula and the sample removal chamber is cleared of tissue particles and fluid. The ejection of the sample when the sample removal chamber is around halfway open is so that the ejection of the tissue sample is assured and the tissue sample does not fall back into the chamber as a result of premature dissipation of the excess pressure. The narrowing of the cavity of the biopsy cannula by the stopper 79, which prevents or impedes tissue from getting into the cavity of the biopsy cannula, proves to be especially advantageous when removing the sample, since the narrower cross section boosts the ejection pressure. The best ejection results, therefore, may be achieved with the sample removal chamber halfway open; i.e., the cutting sheath clears half of the sample removal chamber. The excess pressure also forces tissue fluid out of the sample removal chamber and cleans it.

In the example illustrated in FIG. 5A, the vacuum pressure generating device is arranged in parallel with the biopsy cannula. However, the vacuum pressure generating device may also be arranged lying in the axis of the biopsy cannula or the hand piece; neither does it require its own connection element, if for example it is mounted directly on the end of the biopsy cannula.

The components of the exemplary device shown in FIG. 5A and FIG. 5B are now described in further detail. The gear motor 21 for the cocking mechanism and the cutting sheath is located at the distal lower-left portion of the housing interior, while the actuating mechanism 105 (FIG. 5H) for the vacuum pressure generating device 5 is positioned at distal lower-right portion of the housing interior. In the bottom proximal section is accommodated the energy supply for the actuating motors and the other electrical parts, such as for the control and/or monitoring elements; preferably, batteries or a storage battery are used for this, e.g., a 7.2 V lithium ion battery, 1 Ah. The proximal portion of the housing interior space above the battery compartment, is utilized mainly for the tension slide 28 with locking piece (FIG. 5C); this is connected to a block 26, which is part of the base block 8. The battery compartment is sealed on top by a separation plate.

In the upper-left part of the housing interior there is arranged a biopsy cannula carrier 37, which can be inserted into and taken out from the U-shaped insert holder 36 of the base block 8, which is open at the top, and the bracket 40 arranged on either side of the tension slide 28 and pointing upward; the biopsy cannula/cutting sheath unit with actuating parts is moveably mounted in this, extending for almost the entire length of the hand piece. This means that, in the uncocked state, the distal end surface of the biopsy cannula carrier 37 lies against the distal end cover 6 of the housing, and in the cocked state the proximal end surface lies against the proximal end cover 7. "Almost the entire length" means that the biopsy cannula carrier is at least shorter by the distance required in the interior of the housing for the cocking sequence. If the cocking distance of the tension slide is 20 mm, for example, the biopsy cannula carrier must be able to move by this amount. In this particular design, the cocking distance set at 20 mm. As one of ordinary skill in the art having the benefit of this disclosure would appreciate, the device may be adapted to allow the physician to adjust the device to capture the desired length of the sample.

The cocking device itself consists of a tension slide 28, placed on a bolt 30, the bolt screwing into the base block 8. The bolt 30 has a spiral spring 31 surrounding it. The locking device of the tension slide is secured to the block 26. In the upper-right proximal interior of the housing is accommodated the vacuum pressure generating device 5 with parts of the actuator; the actuating motor with reduction gearing for the vacuum pressure generating device is located in the distal lower-right area of the housing interior.

At the left side of the bottom piece of the housing there is a surface 113 provided for the control interface panel with the operating and monitoring elements (FIG: 5A). The control interface panel secured to the housing is designed as an independent component, which is glued, for example, onto the surface 113 of the bottom piece 9. This control interface panel is connected by lines to other electronic components arranged in the housing, and to the power supply. The board contains in particular switches for the operation and diodes for the monitoring. The activating button for mechanical triggering of the cocked tension slide protrudes through a recess 65 in the bottom piece of the housing and the board.

When configuring the operating and monitoring elements on the control interface panel consideration was given to the difference between the cocking sequence of the tension slide and the triggering of the tension slide, on one hand, and the performance of the biopsy, such as the cutting out of the sample, as well as the removal of the sample with the ejection of the sample, on the other hand. Accordingly, the activating button (trigger) for the tension slide has been placed at the right and the cocking button for cocking the tension slide is at left. The program button for performing the biopsy is in the middle. It is necessary to press the program button for three functions. The first function, start or reset, is indicated by the reset diode, while the sample removal diode arranged underneath indicates the opening and closing of the sample removal chamber when removing the sample. The lowermost eject diode indicates the ejection of the removed sample. The cocking diode indicates the cocking of the tension slide; the locking diode indicates the locking of the tension slide. The battery charge diode indicates the charge condition of the battery or storage battery. The diodes are switched so that the diode blinks while performing the particular sequence and after completion of the sequence the next diode lights up. When there are two possible choices, both diodes are lit. The operator is then free to make a choice. The mode of operation and possibility of control shall be examined more closely in detail when describing the sequence. Symbols (icons) at the margin symbolize the individual processes.

To improve the operating safety it may be advisable to outfit individual automated sequences with delay circuit. In particular, it has been found that the processes of "cocking of the tension slide" by pressing the cocking button and "ejection of sample" by pressing the program button are provided with delay circuits of around 1.2-1.5 seconds to improve the operating safety. Furthermore, the operating safety is improved when the light-emitting diodes indicating the individual processes have different colors for processes outside and processes inside the tissue.

Figure 5D:
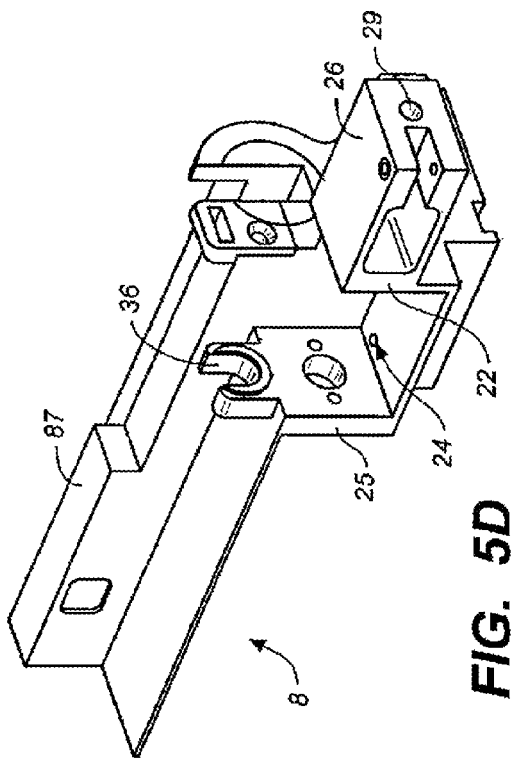
FIG. 5D shows the base block of the biopsy apparatus of FIG. 5A (perspective view).
Figure 5G:
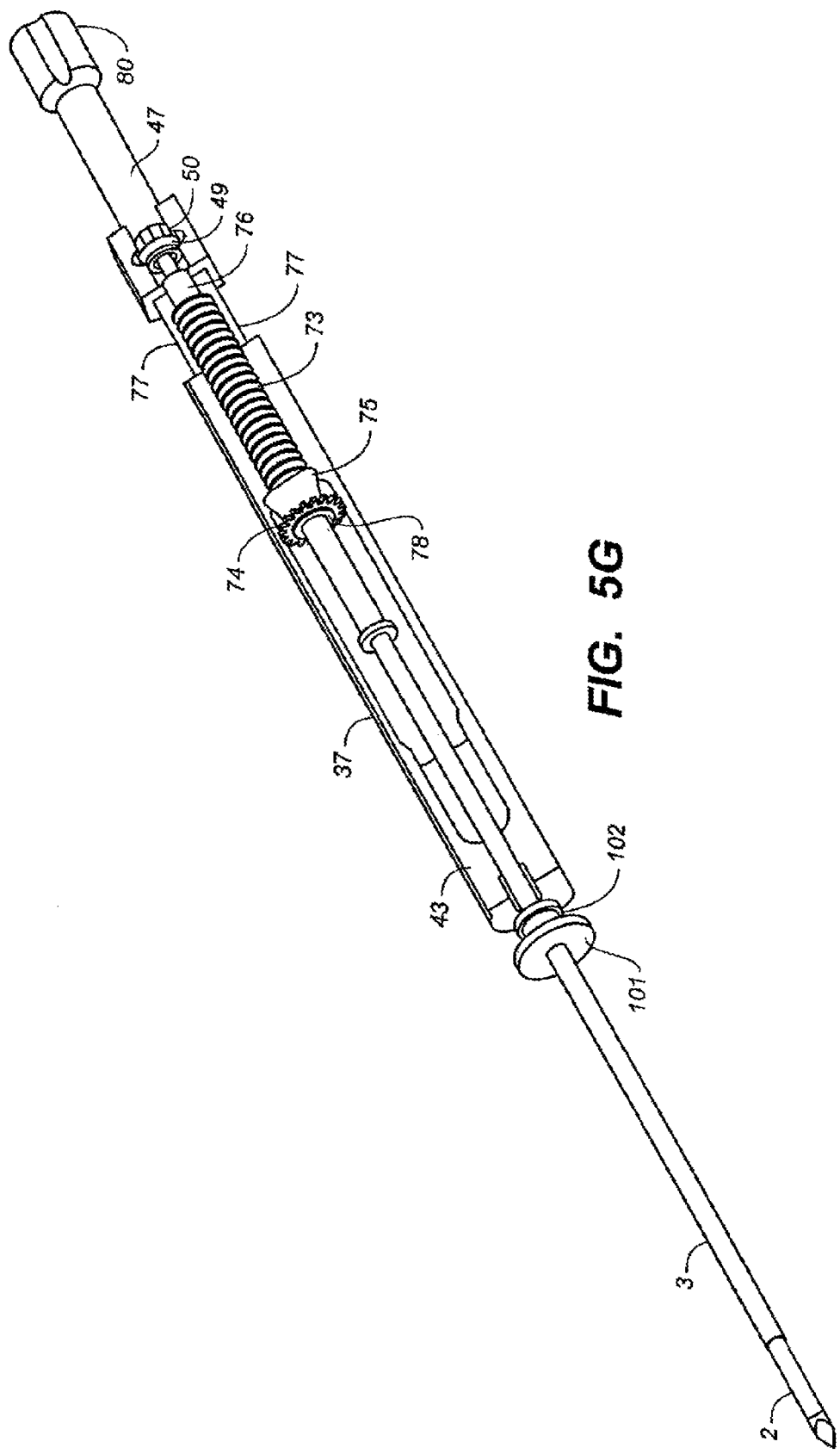
FIG. 5G illustrates the biopsy cannula carrier with press-fitted biopsy cannula/cutting sheath and plastic holder (perspective view).

A perspective representation of the base block 8 is shown in FIG. 5D. The base block 8 can be divided into two halves, looking down the lengthwise direction; the left side serves to secure the joint actuation for cutting sheath and tension slide, and also in its upper part to mount the biopsy cannula carrier; the right side serves to secure the actuation for the vacuum pressure generating device and to mount one side of the vacuum pressure generating device. Between the two actuating motors 21, 58, beneath the center rib 87, is arranged a central electronic system control board. The base block 8 has a U-shaped space 24, in which is installed a toothed roller 23, driven by the gear motor 21. For this, the take-off shaft of the gear motor is mounted or inserted in an opening in the wall 25 of the base block 8. The toothed roller 23 is mounted on the take-off shaft and secured to it, for example, by means of a set screw, so that it cannot turn or shift. At the other end, the toothed roller 23 is mounted in the wall 22 of the base block 8. The actuating motor used is a DC motor with a speed of around 11000 rpm. The DC motor is connected to a planet gear with high reduction ratio (e.g., 67:1), on whose take-off shaft the toothed roller 23 is mounted.

An additional block 26 is machined to form the wall 22, pointing in the proximal direction, which accommodates both the swiveling double lever 33 for the locking process and also serves to fasten the bolt 30 for guiding the tension slide 28. The bolt 30 is screwed into the threaded borehole 29. During the cocking process, the tension slide 28 moves in the proximal direction on the bolt 30 and the separating plate arranged underneath. The spiral spring 31 arranged on the threaded bolt 30 is compressed during the cocking process. At one end, the spiral spring thrusts against an end piece 32 of the threaded bolt or directly against the end cover 7 of the housing; the other end of the spiral spring thrusts against the end of the guide borehole of the tension slide.

The tension slide 28, which adjoins the block 26, is arranged at equal height and is roughly equal in cross section. On its top side, the tension slide has two brackets 40. The upward pointing surface 41 of the tension slide, as well as the upward pointing surface 44 of the block 26, and the upward pointing surface of the extension 42 of the basic block 8, together form a planar bearing surface for the lower sliding surface 43 of the biopsy cannula carrier 37 mounted thereon. The biopsy cannula carrier is made of plastic. As the tension slide is moved from the starting uncocked condition (FIG. 5E) to the cocked condition, i.e., in the proximal direction, the biopsy cannula carrier 37 held by the brackets 40 slides across the surface 42 and 44. It is also conceivable that the sliding surfaces are configured not planar, as in the sample embodiment, but instead have specially configured sliding surfaces; the important thing is that the biopsy cannula carrier 37 can slide easily and straight on the sliding surface and the biopsy cannula can penetrate straight into the tissue, or tumor, after triggering the activation button. Therefore, the upper outer contour of the biopsy cannula carrier is also configured correspondingly to the inner contour of the housing cover and has only slight play relative to the housing cover in order to prevent the biopsy cannula from deviating upward.

FIG. 5B shows the biopsy cannula carrier 37, which can be inserted into the brackets 40 of the tension slide 28 with biopsy cannula 2 and cutting sheath 3, as well as other parts. The hollow, round circular biopsy cannula 2 has a needle tip, which adjoins the sample removal chamber 71 (FIG. 5F). The biopsy cannula 2, which is round in cross section, is surrounded by a coaxially arranged cutting sheath 3, round in cross section, having a cutting edge 72 at its distal end, facing the sample removal chamber, which serves to cut out the tissue sample after the biopsy cannula is introduced (with sample removal chamber closed) and after the sample removal chamber is opened and the sample is sucked into the sample removal chamber. The cutting edge preferably stands perpendicular to the lengthwise axis of biopsy cannula and cutting sheath. The cutting process occurs by rotation and simultaneous lengthwise displacement of the cutting sheath by means of the threaded spindle drive. It is also contemplated that the motion occurs not continuously, but stepwise or vibrating, i.e., the feed process moves back and forth with short intervals. For example, the gear motor 21 is reversed for 2 mm, then reversed again for 2 mm, in a cutting motion that is repeated again before the sample removal chamber 71 is advanced all the way forward and closed. The forward and reverse motion causes the sharpened edge of the cannula 72 to cut the tissue while it is drawn into the sample chamber by the vacuum.

At the other, proximal end of the cutting sheath, away from the cutting edge 72, there is fastened a threaded spindle casing 73 with a gear 74 arranged at the end face of the threaded spindle casing. The threaded spindle casing with gear is arranged on the cutting sheath and prevented from turning and shifting. The threaded spindle cooperates with a threaded spindle nut 75, which is firmly press-fitted in the biopsy cannula carrier 37. The gear 74 lies next to the nut 75, i.e., before the spindle casing begins. When the threaded spindle casing is turned by means of the gear 74, the cutting sheath is rotated and shifted in lengthwise direction along the biopsy cannula 2.

The gear 74 at the distal end of the threaded spindle engages with the toothed roller 23 after the biopsy cannula carrier is inserted in the brackets 40. So as to allow for inserting the biopsy cannula carrier 37 into the brackets of the tension slide when the slide is not cocked (FIG. 5B), the biopsy cannula carrier has two plane parallel recesses 77. When the sliding surface of the biopsy cannula carrier 37 is placed on the surfaces 41, 42 and 44, at the same time the cutting sheath is inserted in the holder 36 of the base block 8. To improve the turning of the spindle drive, especially when the holder 36 is used to support the cocking of the tension slide, a plastic disk 78 may be inserted at the distal side of the gear, being provided with a slight cone. When the biopsy cannula carrier is correctly inserted, it slides to the proximal end by the sliding surface 43 over the surfaces 42 and 41 when the tension slide is cocked. Since the specimen removal chamber is only closed after inserting the biopsy cannula carrier, the gear 74 bears against the holder 36. Now, if the toothed roller 23 is driven further in the same direction, the threaded spindle drive will screw the tension slide in the proximal direction along the biopsy cannula carrier, until it locks; the biopsy cannula will be pulled inward, while the cutting sheath remains in its position. After the locking, the cutting sheath protrudes beyond the tip of the biopsy cannula. Therefore, after the locking of the tension slide, the cutting sheath is rotated back to the starting position (opposite direction of rotation); the gear 74 will move in the proximal direction in the toothed roller. After releasing of the tension slide, the biopsy cannula/cutting sheath with gear slides back towards the distal direction with the biopsy cannula carrier. Now, the cutting sheath can again be moved in the proximal direction in order to open the sample removal chamber.

The proximal end of the cutting sheath is connected to the hollow biopsy cannula by a seal element 76, able to move in rotation, but air-tight, so that neither air can get in between biopsy cannula and the cutting sheath coaxially surrounding it, nor can air escape during excess pressure. On the proximal end of the biopsy cannula 2 is mounted air-tight a round, likewise hollow plastic part 47, being frictionally joined to the biopsy cannula. The plastic part 47 has a bearing element 49 at its distal end, which is press-fitted into the biopsy cannula carrier; at its proximal end, protruding from the hand piece 1, there is inserted another plastic part 112, which can turn relative to the plastic part 47 and the biopsy cannula 2. Between biopsy cannula and plastic part 112 there is inserted an O-ring seal. The plastic part has a plug 17 at its proximal end, onto which the connection element 4 is placed air-tight.

There is also a knurled disk 80 on the proximal end, protruding from the biopsy cannula carrier and the housing, by which, when rotated, the position of the sample removal chamber can be adjusted radially, without altering the position of the cutting sheath. One rotation of the biopsy cannula involves only one rotation of the sample removal chamber and, thus, the sample removal device. The plastic part 47 with biopsy cannula and cutting sheath is press-fitted into the biopsy cannula carrier with the bearing element 49 and the threaded spindle nut 75. The biopsy cannula can rotate in the biopsy cannula carrier and is mounted in the cutting sheath by the bearing element 49 and its narrow guide in the cutting sheath, and it can shift in the lengthwise axis with the biopsy cannula carrier. As described above, the cutting sheath is axially movable by rotation relative to the biopsy cannula. A polygon 50 (positioned proximal of the bearing element 49) is arranged on the plastic part, which can lock with the biopsy cannula carrier by tension, so that the sample removal chamber of the biopsy cannula can be brought into the most favorable position for the biopsy removal and held there by means of the knurled disk 80.

Details of the sample removal chamber and the tip of the biopsy cannula are represented in FIG. 5F. The sample removal chamber 71 adjoining the needle tip is open above for approximately 25% of its cross section. The cutting edges, including the distal circumference of the cutting sheath 3 and the sides of the sample removal chamber 72 on the biopsy cannula, may be grounded or sharpened. The sample removal chamber is between approximately 15 and 25 mm in length. It adjoins the cavity of the biopsy cannula. At the transition, i.e., the proximal end of the sample removal chamber, the cross section of the cavity of the biopsy cannula is closed between approximately 50% and 75% by a narrowing, e.g., a stopper 79. The height of the stopper is chosen such that it extends downward past the recess of the sample removal chamber. In this way, the vacuum will especially draw in the tissue sample through the continuous opening of the sample removal chamber and bring the tissue sample up against the wall of the sample removal chamber.

When there is excess pressure in the cavity of the biopsy cannula, the narrowing or stopper has a pressure boosting effect. The stopper has roughly the length of 10 mm and is glued or welded into the cavity. When using laser welding, it has proven to be advantageous to make the distal side of the stopper thin for a short length, around 2 mm, by removing material at the end surface. As a result, in this region at the end surface the tube of the biopsy cannula is welded to the end surface of the stopper and is air-tight at the end surface. The stopper can also be of shorter length, as long as the same effect is achieved. Thus, the stopper can also be replaced by a lip or a partial plug of approximately the same height. The important thing is that the narrowing is configured such that the vacuum is brought to bear primarily from the bottom in the sample removal chamber, so that the sample clings to the wall of the sample removal chamber during the cutting process and does not change in length. It has also proven to be advantageous to provide additional fixation means on the sample removal wall.

The suctioning of the sample from the bottom into the sample removal chamber produces, first, a high fill ratio of the sample removal chamber and, second, especially due to its configuration, a good fixation of the sample on the wall. Since the cutting sheath separates the sample at the outside of the biopsy cannula, this firm suctioning of the sample into the interior is also preserved during the separation process. Furthermore, due to the cutting sheath arranged on the outside, and the vacuum applied, no tissue is suctioned into the hollow cutting sheath and thus the tissue cannot get twisted or turned by the rotating lengthwise movement of the cutting sheath, as it is held fast in the interior of the cutting sheath. This improves the quality of the sample, since the pathologist obtains original material corresponding to the cross section of the cut and not being twisted or deformed. When the sample is ejected under pressure, a complete cleaning of the sample removal chamber occurs in addition through the stopper 79, so that no commingling occurs when used repeatedly. Since the vacuum generating device is used at the same time as a pressure generating device, the entire cavity is cleaned, especially that of the cannula.

FIG. 5H shows the drive and the installation of the vacuum pressure generating device 5 (view from the rear, i.e., opposite the Z-axis, housing cover and lower housing piece left out). In the upper-right proximal region, the vacuum pressure generating device 5 is arranged as a piston/cylinder unit 69. It consists of a syringe body 52 with threaded spindle 53 arranged inside, at whose end facing the syringe bottom there is fastened a plunger with seal elements—as is commonly known with syringes. At the end of the syringe body 52 facing the base block 8, a threaded spindle nut is arranged on the threaded spindle with a gear 55 formed at the circumference. The threaded spindle nut has one or more thread turns. The threaded spindle 53 interacts with the threaded spindle nut. The spindle has a pitch of around 5 mm per turn, so that at each rotation the plunger is moved out from the syringe body by a precisely defined amount, i.e., away from the syringe bottom, or toward the syringe bottom, depending on the direction of turning.

The toothed crown 55 arranged on the circumference of the threaded spindle nut meshes with the drive pinion 56, which is fastened on the take-off shaft of the DC gear motor 58. The take-off shaft of the DC gear motor 58 is mounted in the base block 8; for this, the take-off shaft is inserted into the transverse plate 59 of the base block. When the DC gear motor 58 is activated, the plunger is moved toward the syringe bottom or in the direction of the base block 8, depending on the direction of turning. The drive motor used is likewise a DC motor with high speed, connected to a planet transmission with high reduction ratio. It corresponds to the motor already described for the cocking mechanism.

The plunger is configured in familiar fashion as a syringe plunger. The syringe body made from plastic, being a cylinder with a bottom, is transparent. In order to prevent a twisting of the threaded spindle 53 upon actuation of the threaded spindle nut, the two opposite surfaces of the threaded spindle are plane in configuration. The threaded spindle is inserted into the insert element by its free end. The spacing between the surfaces of the threaded spindle corresponds to the width of the U-shaped insert element of the base block 8. There is only slight play between the U-shaped cross section of the insert element and the spindle surfaces at either end. The threaded spindle nut thrusts against the base block. In order to prevent the syringe body from sliding out upon turning of the threaded spindle nut, the bearing surface at the base block 8 is slightly conical toward the bottom. The connection piece of the syringe body is inserted into the passage 16 of the proximal end cover 7 so that the syringe body is held in roughly horizontal position. In addition, a pin pressed into the machined aluminum motor block may also be provided to prevent the syringe from rotating. The pin rests against the plastic syringe body when the needle is loaded into the housing properly. When the lid is closed the pin digs into the syringe slightly and prevents the syringe from rotating.

If the syringe plunger is moved beyond the ventilation opening 67 (FIG. 5H)—when the vacuum is no longer required—intake of air (atmospheric pressure) through the ventilation opening 67 will dissipate the previously established vacuum in the hollow biopsy cannula. If, then, the direction of turning of the gear motor is reversed, the vacuum pressure generating device will build up an excess pressure in the system by retraction of the plunger (toward the bottom of the syringe), which brings about the ejection of the tissue sample after opening the sample removal chamber. Moreover, the pressurized air will clean not only the sample removal chamber, but also in particular the inside of the biopsy cannula. The stopper narrowing the cavity of the cannula will make it difficult or entirely prevent tissue parts from getting into the cavity of the biopsy cannula. The narrowing of the cannula cavity by the stopper 79 will increase the pressure at the sample removal chamber and thereby improve the ejection of the sample, even when the sample removal chamber is half open.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A biopsy apparatus, comprising:
a cannula having a lumen, a proximal portion, a closed distal end, and an orifice located on a circumferential surface of the cannula, the orifice being configured to receive a tissue sample into the lumen of the cannula;
a cutting sheath coaxially disposed with the cannula, the cutting sheath being configured to be movable relative to the cannula to selectively cover the orifice;
a pressure chamber coupled to the proximal portion of the cannula, the pressure chamber configured to contain a pressure; and
a bifurcated valve assembly interposed between the cannula and the pressure chamber, the bifurcated valve assembly having a first valve configured to release the pressure into the lumen of the cannula and having a second valve coupled between the first valve and the pressure chamber, the second valve configured to facilitate an inflow of air into the pressure chamber.

2. The biopsy apparatus of claim 1, further comprising:
a first actuator configured to operate the first valve;
a second actuator configured to operate the second valve; and
an electronic system controller coupled to the first actuator and the second actuator configured to selectively control the first valve and the second valve.

3. The biopsy apparatus of claim 1, further comprising:
a first actuator configured to control an opening and a closing of the first valve;
a second actuator configured to control an opening and a closing of the second valve; and
an electronic system controller coupled to the first actuator and the second actuator, and configured to selectively control the opening and the closing of each of the first valve and the second valve.

4. The biopsy apparatus of claim 1, wherein the second valve is further configured to release pressure from the biopsy apparatus.

5. A biopsy apparatus, comprising:
a housing;
a cannula coupled to the housing and having a lumen, a proximal portion, a closed distal end, and an orifice located on a circumferential surface of the cannula, the orifice being configured to receive a tissue sample into the lumen of the cannula;
a cutting sheath coaxially disposed with the cannula, the cutting sheath being configured to be movable relative to the cannula to selectively cover the orifice;
a pressure generating device positioned in the housing and coupled to the proximal portion of the cannula, the pressure generating device defining a pressure chamber, the pressure generating device configured to selectively generate each of a positive pressure and a negative pressure;
a bifurcated valve assembly interposed between the cannula and the pressure generating device, the bifurcated valve assembly including a first valve configured to release pressure into the lumen of the cannula and having a second valve coupled between the first valve and the pressure chamber, the second valve configured to facilitate an inflow of air into the pressure chamber of the pressure generating device, a first actuator configured to operate the first valve, a second actuator configured to operate the second valve, and an electronic system controller coupled to the first actuator and the second actuator configured to selectively control the first valve and the second valve.

6. The biopsy apparatus of claim 5, wherein:
the first actuator is configured to control an opening and a closing of the first valve;
the second actuator is configured to control an opening and a closing of the second valve; and
the electronic system controller is configured to control each of the first actuator and the second actuator to selectively control the opening and the closing of each of the first valve and the second valve.

7. The biopsy apparatus of claim 5, wherein the second valve is further configured to release pressure from the biopsy apparatus.

8. A biopsy apparatus, comprising:
a cannula having a lumen, a proximal portion, a closed distal end, and an orifice located on a circumferential surface of the cannula, the orifice being configured to receive a tissue sample into the lumen of the cannula;
a cutting sheath coaxially disposed with the cannula, the cutting sheath being configured to be movable relative to the cannula to selectively cover the orifice;
a pressure generating device having a cylinder and a piston movable within the cylinder, and configured to selectively generate each of a positive pressure and a negative pressure, the pressure generating device coupled to the proximal portion of the cannula; and a bifurcated valve assembly interposed between the cannula and the pressure generating device, the bifurcated valve assembly having a first valve configured to release one of the positive pressure and the negative pressure into the lumen of the cannula, and having a second valve coupled between the first valve and the pressure generating device, the second valve configured to facilitate an inflow of air into the pressure generating device.

9. The biopsy apparatus of claim 8, further comprising:

a first actuator configured to operate the first valve;

a second actuator configured to operate the second valve; and an electronic system controller coupled to the first actuator and the second actuator configured to selectively control the first valve and the second valve.

10. The biopsy apparatus of claim 8, further comprising:

a first actuator configured to control an opening and a closing of the first valve;

a second actuator configured to control an opening and a closing of the second valve; and an electronic system controller coupled to the first actuator and the second actuator, and configured to selectively control the opening and the closing of each of the first valve and the second valve.

11. The biopsy apparatus of claim 8, wherein the second valve is further configured to release pressure from the biopsy apparatus.

\* \* \* \* \*